United States Patent [19]
Bayol et al.

[11] Patent Number: 4,713,373
[45] Date of Patent: Dec. 15, 1987

[54] XYLAN SULFATES OF LOW MOLECULAR WEIGHT, PROCESS FOR THEIR PREPARATION AND MEDICAMENTS CONTAINING THEM

[75] Inventors: Alain Bayol, Tournefeuille; Francis Blanc, Lattes; Jacqueline Lansen, Montpellier; Jean-Pierre Maffrand; Jean-Marie Pereillo, both of Portet, all of France

[73] Assignee: Sanofi S.A., Paris, France

[21] Appl. No.: 793,657

[22] Filed: Oct. 31, 1985

[30] Foreign Application Priority Data

Nov. 7, 1984 [FR] France .................................. 84 17460

[51] Int. Cl.$^4$ ..................... A61K 31/725; C08B 37/14; C08B 37/00
[52] U.S. Cl. ...................................... 514/54; 514/822; 536/118
[58] Field of Search ................... 536/118; 514/54, 822

[56] References Cited

U.S. PATENT DOCUMENTS 4,524,066  6/1985  Wolf ..................................... 536/118

OTHER PUBLICATIONS

Yasuoka et al., "Chem. Abst.", vol. 82, 1975, p. 93326(s).
Doctor et al., "Chem. Abst.", vol. 99, 1983, p. 82257(v).

*Primary Examiner*—Ronald W. Griffin
*Attorney, Agent, or Firm*—Weiser & Stapler

[57] ABSTRACT

The present invention relates to novel xylan sulfates of average molecular weight comprised between 2000 and 5000 Daltons.

The invention also relates to their process of preparation by fractionation and their use in therapeutics as orally active antithrombotic and hypolipaemic agents.

18 Claims, No Drawings

XYLAN SULFATES OF LOW MOLECULAR WEIGHT, PROCESS FOR THEIR PREPARATION AND MEDICAMENTS CONTAINING THEM

The present invention relates to novel xylan sulfates, to the process for their preparation and to their uses in human and veterinary medicine for their antithrombotic and hypolipemic activity.

In this field of activity, heparin is a mucopolysaccharide of animal origin widely used in human therapy, particularly in the prevention and treatment of venous thromboses and pulmonary embolisms. Commercial heparins are constituted in fact by a mixture of polysaccharides whose molecular weights vary between 3000 and 50,000 Daltons. About 80% of these polymers have a molecular weight comprised between 5000 and 25,000 D and the average molecular weight of the mixture is situated around 16,000 D. These polymers, by reason of their high molecular weight have a bio-availability which is almost null orally and, through this fact, standard heparins are only effective after parenteral administration.

More recently, various searchers have fractionated or fragmented these standard heparins to obtain heparins of low molecular weights (average molecular weight comprised between 4000 and 8000 D) which seem to offer less hemorrhagic and thrombocytopemic risks than standard heparins. Other sulfated polysaccharides have shown, in animal pharmacology and in human clinical use, antithrombotic properties comparable with those of heparin. One of these products, called SP 54 or PZ 68 according to the authors is an xylan polysulfate obtained by controlled sulfation of xylans extracted from oak wood, and they cost very much less than that of heparin.

This product has been marketed for about 20 years for use by the injectable route, particularly in the prevention of post-operative venous thromboses, and orally, particularly in the treatment of atherogenous dyslipemias.

Through its effects on systems of (FISCHER A. M. BARROWCLIFFE T. W. & THOMAS D. P. Thromb Haemost, 1982, 47, (2), 104) (FISHER A. M., MERTON R. E., MARSH N. A., WILLIAMS S., GAFFNEY P. J., BARROWCLIFFE T. W. & THOMAS D. P. Thromb Haemost, 1982, 47, (2), 109) (SCULLY M. F., WEERASINGHE K. M., ELLIS V., DJAZAERI B. & KAKKAR V. V. Thromb Res, 1983, 31, 87) and of fibrinolysis (VINAZZER H., STEMBERGER A., HAAS S. & BLUNEL G., Thromb Res, 1982, 27, 341) on the complementary system (WALB D., LOOS M. & HADDING U.Z Natusforsch, 1971, 26, 403), on the wall of the vessels (PAUL R., HERBERT J. M., HAFFRAND J. P., LANSEN J. & RONCUCCI R., Symposium on Atheroma and Thrombosis, London, July 1983, and on lipid metabolism (ROUFFY J., Mises a jour Cardiol, 1983, 12 (8), 381, this product has in fact interesting antithrombotic and antiatheromatous properties.

Like Heparin, it presents itself in the form of a mixture of polymers (xylan sulfates) of different molecular weights. The analytical definition of such mixtures is still delicate and several researchers have been able to give different results for the same product. Thus, VINAZZER et al. have reported SP 54 a molecular weight of 2000 (Thromb. Res., 1980, 20, 57–68) then of 3000 (Thromb. Res., 1982, 27, 341–352); C. D. ES-QUIVEL et al. (Thromb. Res., 1982, 28, 389–399) have described an average molecular weight of 4000; finally C. SORIA et al. (Thromb. Res., 1980, 19, 455–463) have indicated an average molecular weight of 6000 which has also been published very recently by N. F. SCULLY and V. V. KAKKAR (Biochem. J., 1984, 218, 657).

This disparity in the average molecular weights, is doubtless due to the methods of analysis and to the standards used as well as to the absence of precision on the nature (apparent, by weight, by number) of the molar mass published.

By means of the techniques described below. Applicant has found that SP 54 or PZ 68 which corresponds to the following developed statistical formula:

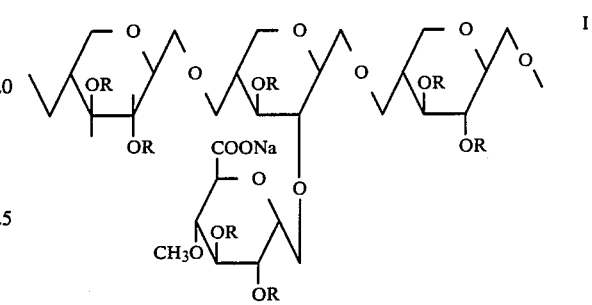

in which R represents the group —SO$_3$Na or hydrogen can be defined in the following manner:

It relates to a mixture of polymers of molar masses comprised between 1000 and 40000 Daltons, having quasi-guassian distribution.

The measurements of parameters of molecular distributions of this product by high performance exclusion chromatography show for different manufacturing batches average values of:

Average number molecular mass or $\overline{Mn}$: 5300 to 5500
Average weight molecular mass or $\overline{Mw}$: 7400 to 7600
Polydispersity index or $D = \overline{Mw}/\overline{Mn}$ measuring the width of the molecular distribution: 1.4 to 1.5.

The apparent average mass or $\overline{Ma}$ which corresponds to the majority isomolecular population in concentration (that is to say the top of the peak on the chromatogram) is comprised between 6500 and 7200 D. The sulfation ratio of the product, that is to say the number of hydroxyl functions esterified by a sulfuric group is accessible through the average determination by weight of the sulfur: 15 to 20%.

It is possible to define also the average degree of sulfation of this mixture of polymers or D.S. as the average number of sulfuric groups per xylose unit concerned as monomeric element.

The average degree of sulfation for the product, accessible by nuclear magnetic resonance of the proton or by microanalytical percentage assays of the carbon and of the sulfur is comprised between 1.5 and 2 and more precisely close to 1.8.

This xylan polysulfate is also characterized by average values of the determinations of pentoses and of glucuronic acids.

Thus the percentage by weight of pentoses expressed as xylose equivalent is 30 to 40%.

The percentage by weight of uronic acids (in fact principally 4 MeO-glucuronic acid) expressed as glucuronic acid varies from 4 to 6%.

This corresponds to a proportion of 1 glucuronic unit per 8 to 10 xylose units.

Applicant has now found that novel xylan sulfates, having a low molecular weight and well - determined physicochemical characteristics, possess good activity by the oral route, with excellent duodenal absorption.

Thus, the present invention relates to xylan polysulfates having the following characteristics:

average degree of sulfation is comprised between 1.5 and 2 apparent average molecular weight $\overline{Ma}$ comprised between 2000 and 5000 Daltons.

ratio by weight of pentoses expressed as xylose comprised between 30 and 40% ratio by weight of uronic acid expressed as glucuronic acid comprised between 0 and 10% the polydispersity indexes of the molecular distributions for the products of the invention are less than or equal to that of the product.

These products only contain negligible amounts of polymers of unit mass higher than 10,000 Daltons.

These xylan sulfates of low molecular weights show a bio-availability by the oral route distinctly higher than that of SP 54 and their duodenal absorption is greater than the gastric absorption. All these observations have led to the development of galenic forms showing good absorption orally in man.

Applicant has finally found that these novel products of the present invention showed, suprisingly a pro-aggregating activity with respect to ADP distinctly higher than that of SP 54 and particularly than heparin, thus permitting less risk of thrombocytopemia to be hoped for than with these products.

These novel xylan polysulfates may be prepared by a process characterized in that the product SP 54 is directly subjected to fractionation by ultra-filtration on membranes or hollow fibers of various porosities.

The analytical characteristics of SP 54 described above and those of the final products have been determined by the following methods:

1

NUCLEAR MAGNETIC RESONANCE SPECTRUM OF CARBON 13

The nuclear magnetic resonnance spectrum of carbon 13 (80 MHz) is obtained on a 10% (m/v) solution in deuteriated water. The chemical displacements of the peaks correspond to the carbon atoms of the sulfated xylose unit and are the following: $C_1$: 100.4 ppm; $C_2$: 73.6 PPM; $C_3$: 74.1 ppm; $C_4$: 75.43 ppm and $C_5$: 60.3 ppm.

2

NUCLEAR MAGNETIC RESONANCE SPECTRUM OF THE PROTON

The nuclear magnetic resonance spectrum of the proton (250 MHz) is produced at the concentration of 20% (m/v) in deuteriated water. The signal corresponding to the water is displaced by the addition of trifluoroacetic acid. The degree of sulfation can be calculated on the basis of the integration of the protons 1 and 3 (5.2 ppm and 4.8 ppm) of the sulfated xylose unit.

3

DETERMINATION OF THE METHOXY GROUPS

The method employed is that described by LAVER M. and WOLFROM M. L. in Methods in Carbohydrate Chemistry Vol. I, page 454, Edited by Ac. Press. 1962.

4

DETERMINATION OF THE URONIC ACIDS

The method employed is that with carbazole of BITTER T. and MUIR H. M. (Anal Biochem, 1962, 4, 330–334).

5

MICRODETERMINATION OF THE SULFUR

After minerlization in a vial according to SHONIGER W. (Mikrochim Acta 1956, 1, 869–876), the sulfur was determined conductimetrically with barium perchlorate.

The centesimal percentages of sulfur and of carbon (obtained by microanalysis) enabled a degree of sulfation or D.S. to be calculated:

number of sulfur moles per 100 g of product: % S/32.06.

number of moles of carbon per 100 g of Product: % C/12.011 number of moles of xylose per 100 g of Product: % C/(12.011×5)

number of sulfate functions per monomeric xylose or $$D.S. = 5 \times \frac{\% S}{\% C} \times \frac{12.011}{32.06}$$

6

DETERMINATION OF THE PENTOSES

The method employed was that with orcinol and ferric chloride in a hydrochloric medium (MEJBAUM W. - Z. Physiol. Chem., 1979, 258, 117) taking xylose as standard.

7

DETERMINATION OF SODIUM SULFATE

It was carried out by high performance liquid chromatography using an IONOSPHER TmA 25 cm long (CHROMPACK ref. 28300) with as eluant 0.7% (m/V) potassium hydrogen phthalate in distilled water. The standardization was carried out with anhydrous sodium sulfate.

8

DETERMINATION OF THE MOLECULAR WEIGHT

It was carried out by exclusion chromatography through two silica columns of porosity 60 Å and 500 Å placed in series. The apparatus used was that of HEWLETT PACKARD 1081 B equipped with a JOBIN and YVON IO refractometer and an HP 79841 A injector. The whole was thermostated at 30° C. The mobile phase containing sodium sulfate was prepared according to BARTH H. G. and SMITH D. A. (J. Chromatogr. 1981,206, 410–415) and modified by adding 0.5% of polyethylene glycol to avoid interactions of the hydrogen bridge type. The ionic strength of the eluant was equal to 1.

The average molecular weights by number ($\overline{Mn}$), by weight ($\overline{Mw}$) and apparent ($\overline{Ma}$) were calculated from a calibration carried out by means of neutral oligosaccharides (xylose, maltotriose) and Dextranes (T40-T70 and T500) according to the method described by YAU W. W. KIRKLAND J. J. and BLY D. D. in Modern size-exclusion Liquid Chromatography page 315 Edited by J. WILEY & SONS (1979).

The polydispersity index was calculated by the ratio $\overline{Mw}/\overline{Mn}$.

The following non limiting examples illustrate the invention:

EXAMPLE 1

Xylan polysulfate fraction or SP 54 of apparent mass 3346 Daltons

A solution of 1800 g of xylan polysulfate in 24 liters of demineralized water (weight/volume concentrations of 7.5%) was ultrafiltered in a system equipped with a ROMICON 22-20 PM 5 hollow fibre cartridge (length 63 cm membrane surface 2.4 m$^2$, cut-off threshold 5000), and a demineralized water intake enabling the mother liquor to be ultrafiltered whilst keeping its volume constant.

The average working pressure upstream of the cartridge was regulated to 1.5 Bar and the average flow rate of ultrafiltrate obtained was of the order of 130 ml/min. When 60 liters of permeate had been withdrawn from the system, the mother liquor retained was withdrawn from the system which was then rinsed with demineralized water. The cartridge used was replaced by ROMICON 15-43 PM 2 (length 63 cm, membrane surface 1.4 m$^2$, cut-off threshold 2000).

The ultrafiltrate solution obtained previously was then concentrated at a pressure of 1.5 Bar to a volume of 19 liters.

The 41 liters of concentrated permeate solution collected from the system were then lyophilized in an industrial apparatus. 189 g of white crystals (10.5% yield with respect to the initial amount of xylan sulfate) was collected.

These crystals, containing the fractions of smallest molecular weight of the initial product and its inorganic impurities (principally sodium sulfate) which were thus found to be concentrated therein, were then desalted in amounts of 3 g on a Trisacryl GF 95 gel column (length 90 cm, diameter 44 mm, distilled water flow rate 3 ml/mm, refractometric detection).

The eluant from the column corresponding to the low molecular weights of xylan polysulfate separated from the eluate portions containing the inorganic impurities were then freeze-dried.

In 10 identical desalting operations, there were collected: 14.2 g of xylan sulfate of low molecular weight free of sodium sulfate.

Yield with respect to the initial amount of xylan sulfate: 5%.

ANALYTICAL CHARACTERISTICS

Molecular distribution $\overline{Mn}=2794$, $\overline{Mw}=3380$, $\overline{D}=1.21$, $\overline{Ma}=3346$.

Chemical composition

Degree of sulfation 1.88 by Sulfa/Carbon microanalysis.

Percentage of Pentoses expressed as xylose: 31.4%.

Percentage of uronic acid expressed in glucuronic acids: 6%.

Content of sodium sulfate: <0.3%.

EXAMPLE 2

Fraction of xylan polysulfate of average molecular weight 3518 Daltons

A solution of 1.5 Kg of xylan polysulfate in 60 liters of permuted water, was ultrafiltered in a system such as that described in example 1 equipped with a ROMICON 15-43 PM 2 membrane (length 63 cm, membrane surface 1.4 m$^2$, cutoff threshold 2000); under 1 Bar pressure, at constant volume.

When 69 liters of ultrafiltrate have been collected the operation is stopped and the system is cleaned for an identical operation.

Permeate solutions of three successive operations namely 180 liters obtained from 3 times 1.5 Kg of xylan polysulfate were then concentrated to 45 liters on the same system equipped this time with a PCAC 1000 millipore spiral model, of cutoff threshold 1000 in cellulose acetate.

When the volume of retentate solution of 45 liters has been obtained (135 liters of concentration ultrafiltrate withdrawn from the system), the permuted water intake was opened to perform a constant volume ultrafiltration. There was withdrawn in this way: 70 liters of ultrafiltrate solution. Then the retentate solution was withdrawn from the system and concentrated in an evaporator under vacuum to a volume of 7 liters. A freeze-drying was then carried out which enabled 402 g of white crystals to be isolated.

Yield with respect to the initial amount of xylan polysulfate (4.5 Kg): 9%.

ANALYTICAL CHARACTERISTICS

Molecular distribution $\overline{Mn}=2732$, $\overline{Mw}=4183$, $\overline{D}=1.53$, $\overline{Ma}=3518$.

Chemical composition

Degree of sulfation: 1.8 by NMR.
Percentage of pentoses expressed as xylose: 30%.
Percentage of uronic acid expressed as glucuronic acid: 4.3%.
Content of sodium sulfate: 2.2%.

EXAMPLE 3

Fraction of xylan polysulfate of apparent average molecular weight 3889 Daltons

A solution of 60 g of xylan polysulfate in 1000 ml of water was ultrafiltered on AMICON HIP 10-8 hollow fibers in a system, with constant volume of retentate.

1100 ml of ultrafiltrate were collected which were concentrated to 800 ml, on the same system equipped with HIP-5-20 hollow fibers (cut-off threshold 5000), then ultrafiltered to constant volume using 4000 ml of distilled water. The 4300 ml of ultrafiltrate collected during the latter operation were concentrated to 800 ml on the same system equipped with a bundle of HIP-2-43 hollow fibers (cut-off threshold 2000) then it was ultrafiltered to a constant volume of retentate by using 1600 ml of distilled water. The retentate was then withdrawn from the system, and freeze-dried. 11.3 g of white powder (19%) as yield were collected.

ANALYTICAL CHARACTERISTICS

Molecular distribution $\overline{Mn}=3330$, $\overline{Mw}=4480$, $\overline{D}=1.34$, $\overline{Ma}=3889$.

Chemical composition

Degree of sulfation: 1.93 by carbon/sulfur microanalysis.
Percentage of pentoses expressed as xylose: 38%.
Percentage of uronic acid expressed as glucuronic acid: 4.9%.

EXAMPLE 4

Fraction of xylan polysulfate of molecular weight 3939 Daltons

A solution of 10 g of xylan polysulfate in 500 ml of distilled water (concentration weight/volume 2%) was ultrafiltered to constant volume on a system equipped with an AMICON HIP-2-43 hollow fiber cartridge of cut-off threshold 2000.

When 1250 ml of ultrafiltrate had been collected the operation was stopped. The sodium sulfate content of this solution was brought back to 1% by concentration and ultrafiltration to constant volume on a system equipped with AMICON 5 YM 2 flat membranes of cut-off threshold 1000.

The final solution was lyophilized and 1.2 g of white crystals were obtained (yield: 12%).

ANALYTICAL CHARACTERISTICS

Molecular distribution $\overline{Mn}=3007$, $\overline{Mw}=4013$, $\overline{D}=1.33$, $\overline{Ma}=3939$.

Chemical composition

Degree of sulfation: 1.85 by NMR.
Percentage of pentoses expressed as xylose: 34.3%.
Percentage of uronic acids expressed as glucuronic acid: 5.1%.
Sodium sulfate content: 1.8%.

EXAMPLE 5

Fraction of xylan polysulfate of average molecular weight 4066 Daltons

A solution of 1 Kg of xylan polysulfate in 33 liters of permuted water (concentration weight/volume 3%) was ultrafiltered in a system equipped with a ROMICON 15-43 PM 2 hollow fibre cartridge (length 63 cm, membrane surface 1.4 m², cut-off threshold 2000) and enabling operation to constant retentate volume under a pressure of 1.2 Bar.

When 50 liters of ultrafiltrate had been obtained the retentate solution was withdrawn.

The system is equipped with a Millipore PCAC 1C spiral module (cellulose acetate, cut-off threshold 1000) to treat the ultrafiltrate solution previously obtained. This solution is concentrated to 42 liters under a pressure of 0.8 Bar, then the water intake enabling the volume of solution treated to be kept constant is opened.

When 63 liters of ultrafiltrate had been collected, the retentate solution withdrawn from the system, its volume was reduced from 42 liters to 8 liters in a vacuum concentrator, then lyophilized. 109 g of white crystals were obtaind (yield: 11%).

ANALYTICAL CHARACTERISTICS

Molecular distribution $\overline{Mn}=3133$, $\overline{Mw}=4716$, $\overline{D}=1.50$, $\overline{Ma}=4066$.

Chemical composition

Degree of sulfation: 1.82 by NMR.
Percentage of pentoses expressed as xylose: 34.5%.
Percentage of uronic acid expressed as glucuronic acid: 4.3%.
Sodium sulfate content: 0.3%.

EXAMPLE 6

Fraction of polysulfate of average molecular weight 4407 Daltons

A solution of 30 g of xylan polysulfate (SP 54) in 1000 ml distilled water was ultrafiltered in a system equipped with a bundle of HIP-5-20 hollow fibers, to a constant retentate volume using 5000 ml of distilled water as continuous addition to the retentate. 5000 ml of ultrafiltrate were collected which were concentrated by means of the same system equipped with HIP 2-43 fibers to 1000 ml. Then it was ultrafiltered to constant retentate volume with continuous addition of distilled water (5000 ml). The retentate was then withdrawn from the system and freeze-dried. 9 g of white powder were collected (30% yield).

ANALYTICAL CHARACTERISTICS

Molecular distribution $\overline{Mn}=3470$, $\overline{Mw}=4570$, $\overline{D}=1.3$, $\overline{Ma}=4407$.

Chemical composition

Degree of sulfation: 1.90 by carbon sulfur microanalysis.
Percentage of pentoses expressed as xylose: 35.8%.
Percentage of uronic acids expressed as glucuronic acids: 4.7%.
Sodium sulfate content: 1.6%.

EXAMPLE 7

Fraction of xylan polysulfate of average molecular weight 4674 Daltons

A solution of 10 g of xylan polysulfate in 500 ml of distilled water (concentration weight/volume 2%) was ultrafiltered in the system permitting operation at constant retentate volume, equipped with a cartridge of AMICON HIP 3-20 hollow fibers (cut-off threshold 3000 Daltons, at a pressure of 0.9 Bars).

When 1250 ml of ultrafiltrate had been withdrawn from the system, the latter solution was concentrated on a system equipped with a Millipore PCAC 1000 flat membrane (cut-off threshold 1000 Daltons) to a volume of 400 ml then ultrafiltered to constant volume.

When 800 ml of ultrafiltrate had been collected, the retentate solution was freeze-dried. 2.7 g white crystals, (yield 27%) were collected.

ANALYTICAL CHARACTERISTICS

Molecular distribution $\overline{Mn}=3648$, $\overline{Mw}=4958$ $\overline{D}=1.36$ $\overline{Ma}=4674$.

Chemical composition

Degree of sulfation: 1.80 by NMR.
Percentage of pentoses expressed as xylose: 35.2%.

Percentage of uronic acids expressed as glucuronic acids: 5.3%.

Content of sodium sulfate: 2.1%.

EXAMPLE 8

Fraction of xylan polysulfate of average molecular 4903 Daltons

A solution of 30 g of xylan polysulfate in 450 ml of distilled water (concentration weight/volume 6.66%) was ultrafiltered to constant retentate volume in a system equipped with an AMICON HIP 5-20 hollow fiber cartridge (cut-off threshold 5000 Daltons) under a pressure of 0.9 Bar. 1200 ml of ultrafiltrate were collected which were retreated on system equipped with a Millipore PCAC 1000 flat membrane.

After concentration to 400 ml, it was ultrafiltered to constant volume. After having collected 600 ml of ultrafiltrate, the retentate was freeze-dried. 8.5 g of white crystals were obtaind (yield 28%).

ANALYTICAL CHARACTERISTICS

Molecular distribution $\overline{Mn} = 4039$, $\overline{Mw} = 5058$, $\overline{D} = 1.25$, $\overline{Ma} = 4903$.

Chemical composition

Degree of sulfation: 1.98 by carbon-sulfa microanalysis.

Percentage of pentoses expressed as xylose: 30.8%.

Percentage of uronic acids expressed as glucuronic acid: 4.6%.

Content of sodium sulfate: 2.3%.

EXAMPLE 9

Fraction of xylan polysulfate of average molecular weight 4921 Daltons

A solution of 2.5 kg of xylan polysulfate in 50 liters of permuted water (concentration weight/volume 2%) was ultrafiltered in a system equipped with a ROMICON 15-43 PM2 cartridge (length 63 cm, membrane surface 1.4 m$^2$, cut-off threshold 2000 Daltons), and with a permuted water intake system enabling operation at constant retentate volume, under a pressure of 850 mBars.

In this way there were withdrawn from the system 31 liters of ultrafiltrate which were desalted then to constant volume, under a pressure of 1.2 Bar on a system equipped with a Millipore PCAC 1000 spiral model (cellulose acetate cut-off threshold 1000 Daltons). After having removed 49.5 liters of ultrafiltrate, the retentate solution was concentrated under vacuum to a volume of 9.2 liters, then freeze-dried. 658 g of white crystals were collected (yield 26%).

ANALYTICAL CHARACTERISTICS

Molecular distribution $\overline{Mn} = 3680$, $\overline{Mw} = 5585$, $\overline{D} = 1.52$, $\overline{Ma} = 4921$.

Chemical composition

Degree of sulfation: 2.0 by NMR.

Percentage of pentoses expressed as xylose: 34.7%.

Percentage of uronic acids expressed as glucuronic acid: 5.7%.

Content of sodium sulfate: 2.3%.

The results of toxicological and pharmacological tests enabled the interesting properties of the products of the invention to be demonstrated.

That is to say of the different fractions which have been obtained from SP 54.

It is therefore an object of the invention to provide a medicament having in particular antithrombotic and hypolipemic properties characterized in that it contains, as active principle, at least one of the fractions prepared by the process of the invention and corresponding to the formula (I).

Toxicological study has shown the low toxicity and the perfect tolerance of the various fractions of the invention. In fact, the tests carried out on the acute chronic, subchronic and delayed toxicity, in different animal species, have not shown any anomaly of any sort. The pharmacological study was done on the anticoagulant, fibrinolytic and lipolytic actions by the oral and introduodenal routes and on the platelet proaggregant activity with respect to ADP, in vitro; these studies were carried in comparison with SP 54.

The anticoagulant activity was determined by the activated cephalin time (CAEN J., LARRIEU M. J., SAMAMA M., In: The hemostasis: method of exploration and practical diagnosis. Ed: l'Expansion Scientifique Francaise, 1975, p.169).

The activated cephalin time (ACT), measures the recalcification of the platelet-freed plasma in the presence of an optimum of lipids (cephalin) and of celite which activates in standardized manner the factors of the contact phase (factors XII, XI, IX). The endogenic prothombinase formation was therefore measured with the exception of the platelet factors replaced by cephalin.

The fibrinolytic activity was measured by the lysis time of the plasmatic euglobulins (KLUFT C. - Haemostasis, 1976,5,136).

The lysis time of the plasmatic euglobulins is a sensitive method enabling the total fibrinolytic action of the SP 54 and of its fractions in the absence of physiological inhibitors of fibrinolysis, removed by dilution and acidification of the plasm, to be evaluated.

The lipolytic activity was measured by the circulating lipase lipo-protein activity (NIKKILA E. A., HUTTUNEN J. K., EHNHOLM C., - Metabolism, 1977, 26, 179).

The determination of the circulating lipase lipoprotein is an indirect measure of the impact of the SP 54 and of its fractions on the metabolism of triglycerides (clarifying power). The enzymatic activity was determined by its capacity to hydrolyze the 14C-triolein substrate into 14C-oleic acid.

Placelet proaggregating activity.

The proaggregating activity of the xylan sulfates was evaluated through their possible capacity to potentiate irreversibly the reversible platelet aggregation induced by low ADP concentrations.

These studies were carried out by the technique of Born on PRP of human origin, the various products to be tested were incubated for 1 min at 37° C. in the presence of PRP.

Increasing concentrations of 2 to 125 μg/ml were used. After this period of incubation, platelet aggregation was induced by weak concentrations of ADP (0.5 to 2 μM causing at least for the controls a reversible aggregation phenomenon.

The results are expressed as minimum concentration of xylan sulfate enabling an irreversible aggregation phenomenon to be obtained.

Reference: G. U. R. Born and J. Cross: The aggregation of blood platelets J. Physiol., 168,178,186).

Introduodenal and oral administration of male rats (Sprague Dawley; Charles River; France) from 200 to 300 g were used. The animals were subjected to a water diet on the eve of the tests.

Pentobarbital anesthesia (50 mg/kg; i.p.) was carried out on all these animals before administration of the different xylan sulfate fractions. The latter were administered at a single dose of 400 mg/Kg.

For the intraduodenal administration, an incision was made at the level of the adbomen. The pylorus and the duodenum were isolated. An incision was made at 1 cm from the plyorus and the products were introduced by means of a tube into the duodenum.

A ligature was made below the incision by means of surgical thread. The oral administration was effected by forced feeding using a stomach tube.

Blood samples were taken for analysis of the various pharmacological parameters from the abdominal aorta respectively one hour after intraduodenal administration and two hours afer oral administration.

They were rendered incoagulable by a 3.8 p. 100 trisodium citrate solution (1 volume of anticoagulant per 9 volumes of blood) or of heparin (250 U/ml of blood) for lipase lipoprotein measurements.

Immediately after the blood sampling, the samples were centrifuged at 2000 x g for 15 minutes at 4° C. for the preparation of the citrated, plasma which is used for the various determinations.

The results are collected in Tables 1 to 6; their statistical analysis was done according to the STUDENT test (group for comparison: SP 54).

TABLE 1

INTRADUODENAL ROUTE
ACTIVATED CEPHALIN TIME

| | | 400 mg/kg | | | |
|---|---|---|---|---|---|
| | | M ± ESM | % | test "t" vs | |
| Product | Ma | sec | (a) | Tem | SP54 |
| CONTROLS | | 20 ± 0,6 | — | — | n.s. |
| Example 1 | 3346 | 32 ± 1,5 | 60 | $p < 0,001$ | $p < 0,001$ |
| Example 2 | 3518 | 32 ± 1,6 | 60 | $p < 0,001$ | $p < 0,001$ |
| Example 3 | 3889 | 24 ± 0,5 | 20 | $p < 0,01$ | $p < 0,01$ |
| Example 5 | 4066 | 28 ± 0,9 | 40 | $p < 0,001$ | $p < 0,001$ |
| Example 6 | 4407 | 29 ± 1,9 | 45 | $p < 0,01$ | $p < 0,01$ |
| Example 8 | 4903 | 24 ± 0,7 | 20 | $p < 0,01$ | $p < 0,05$ |
| Example 9 | 4921 | 29 ± 0,7 | 45 | $p < 0,001$ | $p < 0,001$ |
| SP 54 | 6600 | 21 ± 0,4 | 5 | n.s. | — |

(a): % prolongation

TABLE 2

INTRADUODENAL ROUTE
ANTI-Xa ACTIVITY (YIN TIMES)

| | | 400 mg/kg | | | |
|---|---|---|---|---|---|
| | | M ± ESM | % | test "t" vs | |
| Product | Ma | sec | (a) | Tem | SP54 |
| CONTROLS | | 33 ± 0,6 | — | — | n.s. |
| Example 1 | 3346 | 36 ± 0,5 | 9 | $p < 0,05$ | $p < 0,05$ |
| Example 2 | 3518 | 36 ± 0,3 | 9 | $p < 0,05$ | p 0,05 |
| Example 3 | 3889 | 33 ± 0,3 | 0 | n.s. | n.s. |
| Example 5 | 4066 | 38 ± 0,0 | 15 | $p < 0,01$ | p 0,05 |
| Example 6 | 4407 | 35 ± 1,9 | 6 | n.s. | n.s. |
| Example 8 | 4903 | 33 ± 0,7* | 0 | n.s. | n.s. |
| Example 9 | 4921 | 37 ± 0,4 | 12 | $p < 0,05$ | p 0,05 |
| SP 54 | 6600 | 34 ± 1 | 3 | n.s. | — |

(a): % prolongation

TABLE 3

INTRADUODENAL ROUTE
LYSIS TIME OF THE EUGLOBULINS

| | | 400 mg/kg | | | |
|---|---|---|---|---|---|
| | | M ± ESM | % | test "t" vs | |
| Product | Ma | sec | (a) | Tem | SP54 |
| CONTROLS | | 134 ± 6 | — | — | n.s. |
| Example 1 | 3346 | 102 ± 4 | 24 | $p < 0,01$ | $p < 0,05$ |
| Example 2 | 3518 | 97 ± 4 | 28 | $p < 0,001$ | $p < 0,001$ |
| Example 3 | 3889 | 105 ± 4 | 22 | $p < 0,01$ | $p < 0,05$ |
| Example 5 | 4066 | 93 ± 4 | 30 | $p < 0,01$ | $p < 0,01$ |
| Example 6 | 4407 | 72 ± 2 | 46 | $p < 0,001$ | $p < 0,001$ |
| Example 8 | 4903 | 94 ± 8 | 30 | $p < 0,01$ | $p < 0,05$ |
| Example 9 | 4921 | 99 ± 5 | 26 | $p < 0,01$ | $p < 0,01$ |
| SP 54 | 6600 | 124 ± 8 | 7 | n.s. | — |

(a): % activation

TABLE 4

INTRADUODENAL ROUTE
LIPASE LIPOPROTEIN (L.P.L.)

| | | 400 mg/kg | | | |
|---|---|---|---|---|---|
| | | M ± ESM | % | test "t" vs | |
| Product | Ma | x | (a) | Tem | SP54 |
| CONTROLS | | 3,2 ± 0,3 | 6 | — | $p < 0,001$ |
| Example 1 | 3346 | 14,1 ± 1,6 | 26 | $p < 0,001$ | $p < 0,01$ |
| Example 2 | 3518 | 15 ± 2 | 28 | $p < 0,001$ | $p < 0,01$ |
| Example 3 | 3889 | 7,1 ± 0,8 | 13 | $p < 0,001$ | n.s. |
| Example 5 | 4066 | 15 ± 0,65 | 28 | $p < 0,001$ | $p < 0,01$ |
| Example 6 | 4407 | 3,9 ± 0,7 | 7 | n.s. | $p < 0,01$ |
| Example 8 | 4903 | 8,7 ± 1,1 | 16 | $p < 0,001$ | n.s. |
| Example 9 | 4921 | 15,1 ± 1,5 | 28 | $p < 0,001$ | $p < 0,01$ |
| SP 54 | 6600 | 7,6 ± 0,6 | 14 | $p < 0,001$ | — |

(a): % release
x oleic acid mol/ml/h

TABLE 5

ORAL ROUTE
ACTIVATED CEPHALIN TIME

| | | 400 mg/kg | | | |
|---|---|---|---|---|---|
| | | M ± ESM | % | test "t" vs | |
| Product | Ma | sec | (a) | Tem | SP54 |
| CONTROLS | | 20 ± 0,4 | — | — | — |
| Example 1 | 3346 | 29 ± 0,5 | 45 | $p < 0,001$ | $p < 0,001$ |
| Example 2 | 3518 | 31 ± 0,6 | 55 | $p < 0,001$ | $p < 0,001$ |
| Example 3 | 3889 | 21 ± 0,8 | 5 | n.s. | n.s. |
| Example 5 | 4066 | 29 ± 0,6 | 45 | $p < 0,001$ | $p < 0,001$ |
| Example 6 | 4407 | 21 ± 0,3 | 5 | n.s. | n.s. |
| Example 8 | 4903 | 21 ± 0,8 | 5 | n.s. | n.s. |
| Example 9 | 4921 | 29 ± 0,6 | 45 | $p < 0,001$ | $p < 0,001$ |
| SP 54 | 6600 | 20 ± 0,4 | 0 | n.s. | — |

(a): % prolongation

TABLE 6

PROAGREGANT ACTIVITY RELATIVE TO ADP

| Product | Ma | Critical concentration[a] of sulfated polysaccharides in μg/ml |
|---|---|---|
| Example 1 | 3346 | >125 |
| Example 2 | 3518 | 125 |
| Example 3 | 3889 | ≧125 |
| Example 5 | 4066 | >125 |
| Example 6 | 4407 | >125 |
| Example 8 | 4903 | >125 |
| Example 9 | 4921 | >125 |
| SP 54 | 6600 | 30 |
| Heparin | 19800 | 6 |

[a]Critical concentration = minimum concentration of sulfated polysaccharides enabling the production of an irreversible aggregation phenomenon with ADP on human PRP.

The preceding results show the interesting antithrombotic hypolipemic properties of the products of the invention.

By reason of their low moelcular weight, the latter show in fact, orally and especially intraduodenally, activities higher than those of SP 54 from which they are derived.

For each route and each product, these effects are all the more distinct as the molar mass is smaller in the area claimed.

Thus, the product described in Example 1 causes, at the dose of 400 mg/kg intraduodenally, a prologation by 60% of the activated cephalin time (ACT) whereas SP 54, under the same conditions, does not show any significant activity.

Finally, conversely to SP 54 and especially heparin, the products of the invention practically do not potentiate the in vitro aggregation of human platelets stimulated with ADP. These results therefore allow less thrombocytopenia risks to be hoped for than with the reference product.

The medicament of the invention may be presented in forms administrable by the oral, parenteral, rectal and local routes.

Each unit dose contains advantageously from 0.030 g to 0.250 g of active principle, and the daily administrable dose can vary from 0.030 g to 1000 g according to the seriousness of the disorder treated and the route of administration.

There will be given below, by way of non limiting example, some pharmaceutical formulations of the medicament of the invention.

| 1 - Tablets Dosed with 250 mg of active principle | |
|---|---|
| Active principle (fraction of Example 1) | 250 mg |
| Lactose | 50 mg |
| Cellulose excipient | 60.1 mg |
| Magnesium stearate | 9 mg |
| Silicon dioxide | 0.8 mg |
| Aluminium indigotin lacquer | 0.1 mg |

For a 370 mg finished bare tablet.

For the previously mentined form, it is possible to effect a gastrosoluble coating or a gastroresistant coating of which the formulae are as follows:

| Gastrosoluble film coating | |
|---|---|
| Butyl and dimethylaminoethyl polymethylacrylate, granulated | QS |
| Industrial pharmaceutical isopropanol | QS |
| Acetone | QS |
| Dibutyl phthalate | QS |
| Silicic acid | QS |
| Gastroresistant film coating | |
| Powdered, type 1, anionic polymethylacrylate | QS |
| Industrial pharmaceutical isopropanol | QS |
| Acetone | QS |
| Dibutyl phthalate | QS |
| 2 - Capsules | |
| Active principle (fraction of Example 6) | 0.075 g |
| Excipient q.s.p. | 1 capsule |
| 3 - Injectable solutions | |
| Active principle (fraction of Example 5) | 0.100 g |
| Isotonic solvent q.s.p. | 1 ampule of 2 g |
| 4 - Ointment | |
| Active principle (fraction of Example 9) | 0.150 g |
| Excipient q.s.p. | 1 tube of 30 g |

By their action on the different stages of blood coagulation and fibrinolysis, these medicaments may be used with profit, in prolonged and repeated cures in the preventive or curative treatment of veinous or arterial thromboembolic accidents in the case of phlebitis, pulmonary embolisms and other clinical situations of the same type, angina pectoris, myocardiac infarction, chronic arteritis of the lower limbs, superficial circulatory disorders and ulcers of the limbs.

They may also be used to prevent thromboses in extacorporeal systems (renal hemodialyses).

In addition, their action on lipoprotein-lipase (clearing factor) renders them particularly useful in the treatment of atherogenous dyslipemias.

Finally, these medicatments may also be used advantageously in the treatment of certain inflammatory disorders, such as rheumatoid polyarthritis, arthroses and osteoarthrites.

We claim:

1. Xylan sulfates having an average degree of sulfation of from 1.5 to 2, from 0 to 10 percent uronic acid, from 30 to 40 percent pentoses and an average molecular weight of from 2000 to 5000 daltons.

2. The xylan sulfates of claim 1 having a 1.88 degree of sulfation, 6 percent uronic acid, 31.4 percent pentoses and an average molecular weight of 3346 daltons.

3. The xylan sulfates of claim 1 having a 1.8 degree of sulfation, 4.3 percent pentoses and an average molecular weight of 3518 daltons.

4. The xylan sulfates of claim 1 having a 1.93 degree of sulfation, 4.9 percent uronic acid, 38 percent pentoses and an average molecular weight of 3889 daltons.

5. The xylan sulfates of claim 1 having 1.85 degree of sulfation, 5.1 percent uronic acid, 34.3 percent pentoses and an average molecular weight of 3939 daltons.

6. The xylan sulfates of claim 1 having 1.82 degree of sulfation, 4.3 percent uronic acid, 34.5 percent pentoses and an average molecular weight of 4066 daltons.

7. The xylan sulfates of claim 1 having 1.90 degree of sulfation, 4.7 percent uronic acid, 35.8 percent pentoses and an average molecular weight of 4407 daltons.

8. The xylan sulfates of claim 1 having 1.80 degree of sulfation, 5.3 percent uronic acid, 35.2 percent pentoses and an average molecular weight of 4674 daltons.

9. The xylan sulfates of claim 1 having 1.98 degree of sulfation, 4.6 percent uronic acid, 30.8 percent pentoses and an average molecular weight of 4903 daltons.

10. The xylan sulfates of claim 1 having 2.0 degree of sulfation, 5.7 percent uronic acid, 34.7 percent pentoses and an average molecular weight of 4921 daltons.

11. A therapeutic composition with antithrombotic and hypolipemic activity which comprises a therapeutically acceptable carrier and an effective amount of the xylan sulfates of claim 1.

12. The therapeutic composition of claim 11 which is suitable for oral administration.

13. The therapeutic composition of claim 11 which is suitable for parenteral administration.

14. The therapeutic composition of claim 11 which is suitable for rectal administration.

15. The therapeutic composition of claim 11 which is suitable for local administration.

16. The therapeutic composition of claim 11 which is in the form of a unit dose containing from 0.030 g to 1.00 g of a active principle.

17. A process for the preparation of xylan sulfates having a degree of sulfation from 1.5 to 2, from 10 percent uronic acid, from 30 to 40 percent pentoses and an average molecular weight of from 2000 to 5000 daltons which process comprises mixing xylan sulfates having a molecular weight in the range of 1,000 to 40,000 daltons in a liquid medium, separating the liquid medium which contains the xylan sulfates having a molecular weight of greater than about 2,000 daltons and less than about 5,000 daltons, removing the liquid medium, and obtaining xylan sulfates having molecular weight of from 2,000 to 5,000 daltons.

18. The process of claim 17 wherein the liquid medium containing xylan sulfates having a molecular weight greater than about 2,000 daltons and less than about 5,000 daltons is separated by the ultrafiltration steps of (1) passing the liquid medium through a membrane having a cutoff threshold of 5,000 and (2) passing the liquid medium through a membrane having a cutoff threshold of 2,000 daltons.

* * * * *